US008865915B2

(12) United States Patent
Linol et al.

(10) Patent No.: US 8,865,915 B2
(45) Date of Patent: Oct. 21, 2014

(54) PROCESS FOR THE PREPARATION OF THE L-ARGININE SALT OF PERINDOPRIL

(71) Applicant: Les Laboratoires Servier, Suresnes Cedex (FR)

(72) Inventors: Julie Linol, Malaunay (FR); Stéphane Laurent, Valliquerville (FR); Arnaud Grenier, Breaute (FR); Sébastien Mathieu, Montivillers (FR)

(73) Assignee: Les Laboratoires Servier, Suresnes Cedex (FR)

( * ) Notice: Subject to any disclaimer, the term of this patent is extended or adjusted under 35 U.S.C. 154(b) by 0 days.

(21) Appl. No.: 13/733,353

(22) Filed: Jan. 3, 2013

(65) Prior Publication Data
US 2013/0178635 A1 Jul. 11, 2013

(30) Foreign Application Priority Data

Jan. 5, 2012 (FR) ...................... 12 00034

(51) Int. Cl.
*C07C 277/08* (2006.01)
*C07D 209/42* (2006.01)
(52) U.S. Cl.
CPC ............ *C07D 209/42* (2013.01); *C07C 277/08* (2013.01)
USPC ...................................... 548/452
(58) Field of Classification Search
CPC ............................ C07C 277/08; C07D 209/42
See application file for complete search history.

(56) References Cited

U.S. PATENT DOCUMENTS

| 4,914,214 | A * | 4/1990 | Vincent et al. ............... 548/492 |
| 6,696,481 | B2 * | 2/2004 | Damien et al. ............... 514/412 |
| 7,846,961 | B2 * | 12/2010 | Coquerel et al. ............. 514/412 |
| 2008/0071094 | A1 * | 3/2008 | Joshi et al. ................... 548/452 |
| 2009/0203758 | A1 * | 8/2009 | Coquerel et al. ............. 514/412 |

FOREIGN PATENT DOCUMENTS

| EP | 1279665 | 1/2003 |
| EP | 1664937 | 12/2007 |
| EP | 2161257 | 3/2010 |
| WO | WO 2007 099216 | 9/2007 |
| WO | WO 2007 099217 | 9/2007 |
| WO | WO 2009 157018 | 12/2009 |

OTHER PUBLICATIONS

Frenche Preliminary Search Report for FR1200034 of Jun. 11, 2012.

* cited by examiner

*Primary Examiner* — Nyeemah A Grazier
(74) *Attorney, Agent, or Firm* — Hueschen and Sage

(57) ABSTRACT

Process for the preparation of the compound of formula (I):

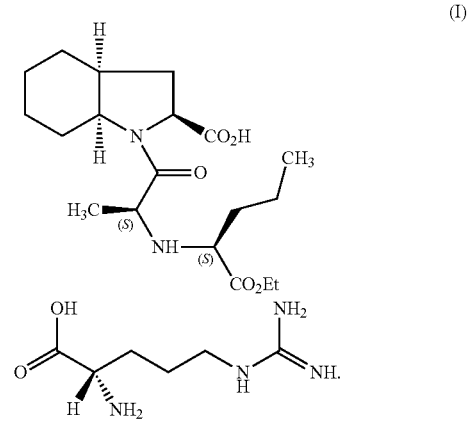

8 Claims, 1 Drawing Sheet

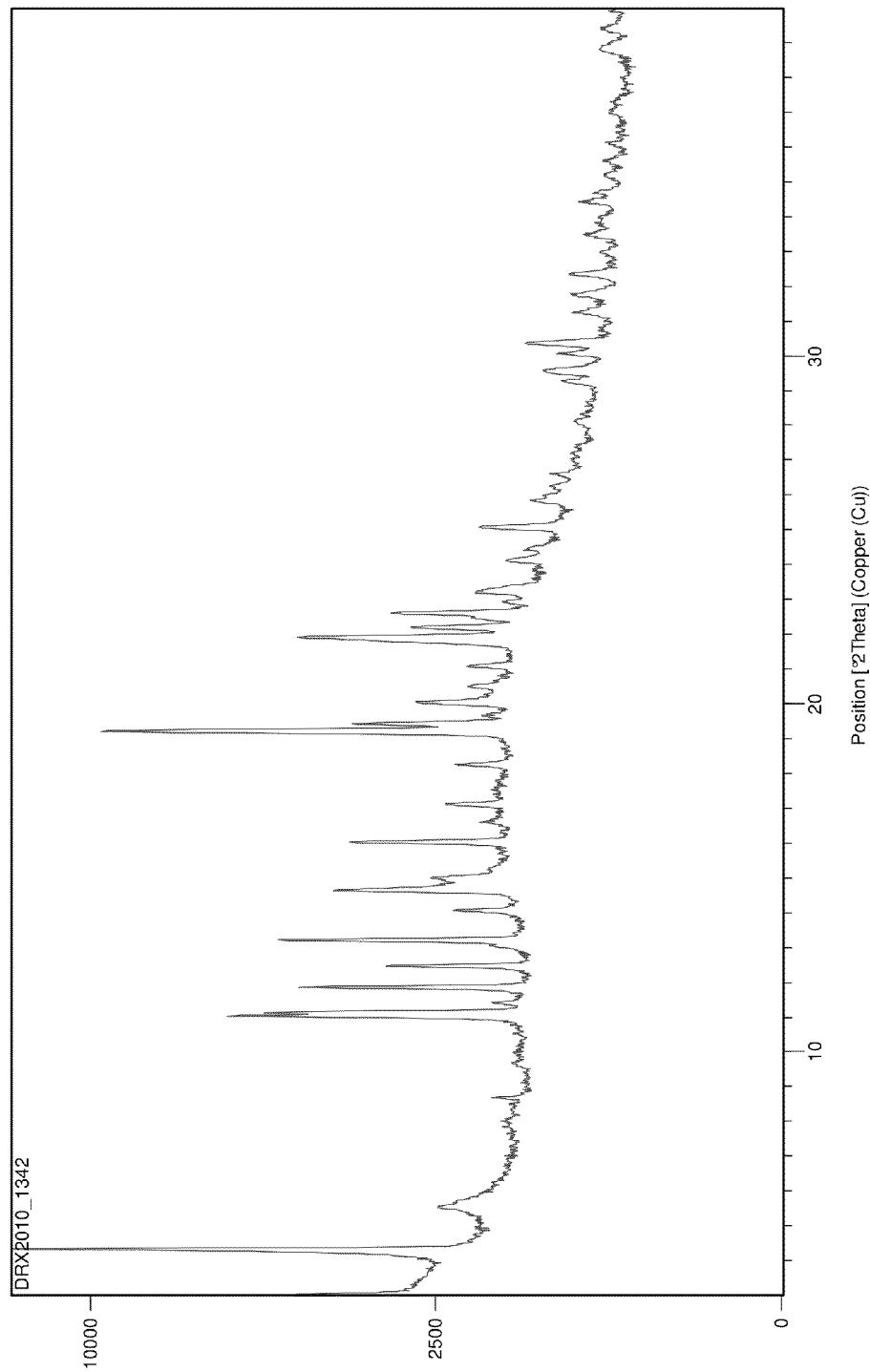
Figure no. 1: Diffractogram of the delta form of perindopril L-arginine

PROCESS FOR THE PREPARATION OF THE L-ARGININE SALT OF PERINDOPRIL

The present invention relates to a process for the preparation of perindopril L-arginine salt of formula (I):

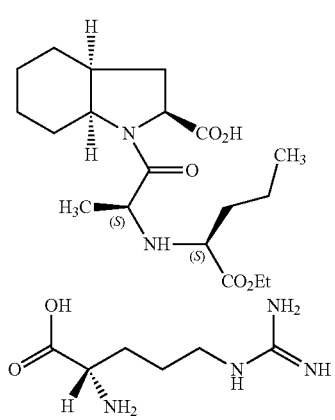

Perindopril and its pharmaceutically acceptable salts, and more especially its L-arginine salt, have valuable pharmacological properties.

Their principal property is that of inhibiting angiotensin I converting enzyme (or kininase II), which makes it possible to prevent, on the one hand, conversion of the decapeptide angiotensin I to the octapeptide angiotensin II (a vasoconstrictor) and, on the other hand, degradation of bradykinin (a vasodilator) to an inactive peptide.

Those two actions contribute to the beneficial effects of perindopril in cardiovascular diseases, more especially in arterial hypertension, heart failure and stable coronary disease.

Perindopril, its preparation and its use in therapeutics have been described in European Patent specification EP 0 049 658.

The L-arginine salt of perindopril was first described in European Patent specification EP 1 354 873.

The alpha and beta crystalline forms of the L-arginine salt of perindopril have been described in European Patent specifications EP 1 989 182 and EP 2 016 051.

The gamma crystalline form of the L-arginine salt of perindopril has been described in Patent Application WO 2009/157018.

In view of the pharmaceutical value of perindopril L-arginine, it was of great importance to obtain it in a good yield and with excellent purity.

More especially, the problem consisted both of finding conditions under which conversion of perindopril into a salt with L-arginine takes place correctly and of readily isolating the L-arginine salt of perindopril from the reaction mixture.

Indeed, most of the tests carried out by the Applicant in order to obtain the L-arginine salt of perindopril starting from perindopril and L-arginine resulted in a product of gelatinous appearance which was very difficult to process subsequently.

Patent specification EP 1 279 665 describes a method of obtaining perindopril salts, more specifically the tert-butylamine salt. The method described allows coupling of the N-[1-(S)-ethoxycarbonyl-butyl]-(S)-alanine moiety to the (2S,3aS,7aS)-2-carboxyperhydroindole moiety whilst avoiding the cyclisation impurities that customarily result from peptide coupling. The tert-butylamine salt of perindopril is accordingly obtained in Example 3 of EP 1 279 665 in a good yield (80%) and with excellent purity (99%).

The Applicant applied the process described in Example 3 of EP 1 279 665 to preparation of the L-arginine salt of perindopril. However, replacing the tert-butylamine with (L)-arginine and otherwise following the procedure of EP 1 279 665 did not make it possible to obtain the L-arginine salt of perindopril in a good yield (see Comparison Example A).

Surprisingly, when conversion into a salt is instead carried out in a solvent system selected from acetonitrile/dimethyl sulphoxide, ethyl acetate/dimethyl sulphoxide and acetonitrile/dimethyl sulphoxide/toluene, the L-arginine salt of perindopril is then obtained in a good yield and with excellent purity, and isolation is greatly facilitated.

More specifically, the present invention relates to a process for the preparation of the L-arginine salt of perindopril by means of reaction between perindopril and L-arginine in a solvent system selected from:
- a binary mixture of acetonitrile and dimethyl sulphoxide,
- a binary mixture of ethyl acetate and dimethyl sulphoxide,
- a ternary mixture of acetonitrile, dimethyl sulphoxide and toluene, at a temperature from 10 to 100° C., preferably from 40 to 80° C.,
followed by isolation by means of filtration of the L-arginine salt thereby obtained.

In accordance with an embodiment of the present invention, the perindopril (free acid) used in the reaction is obtained by reaction of N-[1-(S)-ethoxycarbonyl-butyl]-(S)-alanine of formula (II):

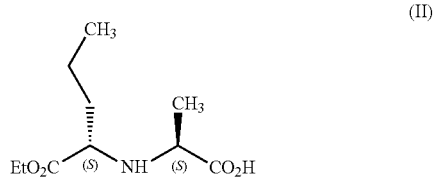

with an activation agent, preferably N,N'-carbonyldiimidazole, phosgene, triphosgene, (1,1'-carbonyldi(1,2,4-triazole) or di(N-succinimidyl) carbonate,
in an organic solvent or a system of organic solvents, preferably acetonitrile, ethyl acetate or dichloromethane,
at a temperature from −20° C. to 80° C., preferably from −10 to 40° C., followed by reaction of the intermediate compound of formula (III) thereby obtained:

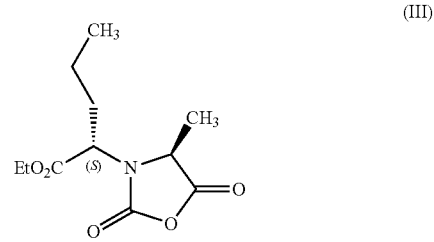

with (2S,3aS,7aS)-2-carboxyperhydroindole,
at a temperature from 0° C. to 80° C., preferably from 5 to 40° C.

An "activation agent" is understood to mean a compound of formula $X_2C=O$ wherein X represents a leaving group such as, for example, a halogen atom or a tosylate, mesylate, imidazolyl, 1,2,4-triazolyl, succinimidyl or optionally substituted alkoxy group.

When the activation agent is N,N'-carbonyldiimidazole, the amount of N,N'-carbonyldiimidazole is preferably between 0.8 and 1.2 moles, inclusive, per mole of N-[1-(S)-ethoxycarbonyl-butyl]-(S)-alanine.

The amount of (2S,3aS,7aS)-2-carboxyperhydroindole is preferably between 0.8 and 1.2 moles, inclusive, per mole of N-[1-(S)-ethoxycarbonyl-butyl]-(S)-alanine.

In accordance with another embodiment of the present invention, the perindopril (free acid) used in the reaction is obtained by desaltification of perindopril tert-butylamine by the action of an acid.

"Desaltification of perindopril tert-butylamine" is understood to mean returning it to perindopril in the form of the free acid.

The following Example illustrate the invention.

These Examples do not all result in the pure delta crystalline form.

Abbreviations:
CDT (1,1'-CarbonylDi(1,2,4-Triazole))
DMSO Dimethyl sulphoxide
DSC (Di(N-Succinimidyl) Carbonate)
HPLC High Performance Liquid Chromatography The filtrations are expressed in standard manner: in terms of kg of liquor filtered per hour and per $m^2$ of filtration area.

EXAMPLE 1

L-Arginine Salt of Perindopril—Starting from Perindopril (Free Acid), in a Binary Mixture of Acetonitrile/DMSO 25/75 Without Seeding Perindopril (12.5 g, 1 eq.) and L-arginine (5.32 g-0.9 eq) are suspended in a mixture of acetonitrile (20 g, d=0.787) and DMSO (61 g, d=1.100). The reaction mixture is heated at 50° C. overnight. The product is then isolated by filtration over a frit. The filter cake is washed and dried.

Perindopril arginine (14.5 g) is obtained in a yield of 79% relative to the perindopril. The crystalline phase isolated is the delta phase. The HPLC quality of the isolated product is greater than 99.0%.

The filtration rate of the mother liquors is of the order of 6000 kg/h/$m^2$.

The L-arginine salt of perindopril thereby obtained is in the delta crystalline form. This form has the following X-ray powder diffraction diagram, measured using a diffractometer with a copper anticathode and expressed in terms of interplanar spacing d, Bragg's angle 2 theta, and relative intensity expressed as a percentage in relation to the most intense line:

| Angle 2 theta (°) | Interplanar spacing d [Å] | Relative intensity [%] |
|---|---|---|
| 4.34 | 20.37 | 66.2 |
| 5.57 | 15.86 | 5.2 |
| 11.04 | 8.02 | 57.5 |
| 11.15 | 7.94 | 47.5 |
| 11.87 | 7.454 | 35.0 |
| 12.47 | 7.09 | 17.9 |
| 13.21 | 6.70 | 33.6 |
| 14.06 | 6.30 | 6.6 |
| 14.64 | 6.05 | 31.8 |
| 16.03 | 5.53 | 17.5 |
| 17.11 | 5.18 | 5.6 |
| 18.27 | 4.85 | 4.1 |
| 19.23 | 4.61 | 100 |
| 19.44 | 4.57 | 17.8 |
| 20.04 | 4.43 | 13.6 |
| 21.11 | 4.21 | 3.7 |
| 21.93 | 4.05 | 23.0 |
| 22.20 | 4.00 | 16.9 |
| 22.61 | 3.93 | 21.2 |
| 23.21 | 3.83 | 4.5 |
| 24.30 | 3.66 | 2.3 |
| 25.09 | 3.55 | 9.4 |
| 25.95 | 3.43 | 1.7 |
| 29.54 | 3.02 | 4.2 |

Each line is considered to have an accuracy of ±0.2° in 2-theta.

FIG. 1: Diffractogram of the delta form of perindopril L-arginine.

EXAMPLE 2

L-arginine Salt of Perindopril—Starting from Perindopril (Free Acid), in a Binary Mixture of Acetonitrile/DMSO 25/75 with Seeding Perindopril (100 g, 1 eq.) and L-arginine (42.6 g, 0.9 eq.) are suspended in a mixture of acetonitrile (220 g, d=0.787) and dimethyl sulphoxide (630 g, d=1.100). The reaction mixture is heated at 70° C. for 3 hours and seeded with 2% of the delta phase, and it is then cooled to 40° C. over 1 hour. The mixture is held at 40° C. for 18 hours with stirring and is then cooled to 20° C. over 1 hour. The product is then isolated by filtration. The filter cake is washed and dried.

Perindopril (L)-arginine (119 g) is obtained in a yield of 79% relative to the perindopril. The HPLC quality of the isolated product is greater than 99.0%.

The filtration rate of the mother liquors is about 6000 kg/h/$m^2$.

EXAMPLE 3

General procedure for production of perindopril (free acid) starting from (2S,3aS,7aS)-2-carboxy-perhydroindole and N-[1-(S)-ethoxy-carbonyl-butyl]-(S)-alanine by activation with N,N'-carbonyldiimidazole N-[1-(S)-ethoxycarbonyl-butyl]-(S)-alanine (65 g, 1 eq.) and N,N'-carbonyldiimidazole (48 g, 1 eq.) are introduced and then acetonitrile (500 g) is added. The reaction mixture is then stirred at a temperature less than +10° C. for 3 hours.

The reaction mixture is poured into (2S,3aS,7aS)-2-carboxyperhydroindole (50 g, 1 eq.); an amount of fresh acetonitrile (80 g) is used to rinse the apparatus.

The reaction mixture is then stirred for 5 hours at a temperature less than +10° C. and is then clarified over a filter to obtain a clear solution.

EXAMPLE 4

L-arginine salt of perindopril—starting from (2S,3aS,7aS)-2-carboxy-perhydroindole, in a binary mixture of acetonitrile/DMSO 50/50 with seeding Perindopril L-arginine (110 g) is obtained by pouring the solution, in acetonitrile, of perindopril (100 g of product) synthesised according to the general procedure of Example 3 into a suspension of L-arginine (44.3 g, 0.85 eq.) in DMSO (540 g, d=1.100) at 50° C.; the reaction mixture is seeded with 2% of the delta crystalline form (compound of Example 1). The mixture is maintained at 50° C. for 15 hours, with stirring, and is then cooled to 20° C. at a rate of 0.5° C./min. The suspension is filtered using a filtration cell. The yield is 75% relative to the perindopril used. The quality of the isolated product is greater than 99.0% according to HPLC.

The filtration rate of the mother liquors is about 5000 kg/h/m².

EXAMPLE 5

L-arginine salt of perindopril—starting from (2S,3aS,7aS)-2-carboxy-perhydroindole, in a binary mixture of acetonitrile/DMSO 75/25 with seeding Perindopril L-arginine (42 g) is obtained by pouring the solution, in acetonitrile, of perindopril (38 g of product) synthesised according to the general procedure of Example 3 by adding L-arginine (17 g, 0.85 eq.) suspended in dimethyl sulphoxide (78 g) at a temperature of 40° C. and after seeding with 4% by weight of perindopril L-arginine in delta form (compound of Example 1). Filtration is carried out at 40° C. using a filtration cell.

The yield is 73% relative to the perindopril used. The quality of the isolated product is greater than 99.0% according to HPLC.

The filtration rate of the mother liquors is about 5700 kg/h/m².

EXAMPLE 6

L-arginine salt of perindopril—starting from (2S,3aS,7aS)-2-carboxy-perhydroindole and triphosgene N-[1-(S)-ethoxycarbonyl-butyl]-(S)-alanine (20 g, 1 eq.) and Na₂HPO₄.12 H₂O (43 g, 1.3 eq.) are suspended in dichloromethane (212 g). The reaction mixture is heated to reflux and then a solution of triphosgene (9.55 g, 0.35 eq.) in dichloromethane (64 g) is poured in. After liquid/liquid washings of the organic phase with water, the dichloromethane is evaporated off to yield activated N-[1-(S)-ethoxycarbonyl-butyl] S)-alanine of formula (III) (22 g). The latter is then dissolved in acetonitrile (180 g). The solution is poured into (2S,3aS, 7aS)-2-carboxyperhydroindole (15 g, 1 eq.) and the reaction mixture is stirred for about 5 hours in the presence of triethylamine (9.15 g, 1 eq.) at a temperature less than 10° C., and it is then clarified through a filter in order to obtain a clear solution. The L-arginine salt of perindopril is obtained by adding L-arginine (14.5 g, 0.90 eq.) suspended in DMSO (180 g) at a temperature of 50° C. After a contact time of about 5 hours, the mixture is seeded with 2% of the delta form and is then stirred overnight at 50° C. and filtered using a filtration cell.

Perindopril L-arginine (43 g) is obtained in a yield of 89% relative to the (2S,3aS,7aS)-2-carboxyperhydroindole (seed subtracted). The HPLC quality of the isolated product is greater than 99%.

The filtration rate of the mother liquors is about 2000 kg/h/m².

EXAMPLE 7

L-Arginine Salt of Perindopril—Starting from Perindopril Tert-Butylamine, in a Ternary Mixture of Acetonitrile/Dimethyl Sulphoxide/Toluene 30/40/30, with Seeding Suspend perindopril tert-butylamine (103 g, 1.00 eq.) and sodium chloride (5.84 g) in toluene (268 g, d=0.867). Stir at ambient temperature.

Add a solution of hydrochloric acid (57.8 mL, #4 N, 1 eq.). Stir for 40 minutes at ambient temperature. Separate the toluene phase from the aqueous phase.

Wash the aqueous phase with toluene (2×90 g, d=0.867).

At this stage, the perindopril is in solution in the toluene at a concentration of 16% w/w.

L-arginine (36.6 g, 0.90 eq.) and dimethyl sulphoxide (566 g, d=1.100) are added and the reaction mixture is heated at 50° C. for 5 hours. Acetonitrile (405 g, d=0.787) is added and the reaction mixture is seeded with 2% by weight of perindopril L-arginine in the delta form (compound of Example 1).

The suspension is stirred for 17 hours; the temperature is then brought to 30° C. over 30 minutes. After stirring for 2 hours, the product is isolated by filtration. The filter cake is washed and dried.

Perindopril L-arginine (95 g) is obtained in a yield of 75% relative to the perindopril tert-butylamine. The HPLC quality of the isolated product is greater than 99.8%.

The filtration rate of the mother liquors is about 4000 kg/h/m².

EXAMPLE 8

L-Arginine Salt of Perindopril—Starting from Perindopril (Free Acid), in a Ternary Mixture of Acetonitrile/DMSO/Toluene 30/40/30, with Seeding Lyophilised perindopril (8.3 g, 1 eq.) is dissolved in a mixture of toluene (43 g) and DMSO (55 g). L-arginine (3.9 g, 1 eq.) is introduced in the form of a suspension in acetonitrile (40 g), and the entire batch is heated at 50° C.

The reaction mixture is seeded with 3% of perindopril arginine in the delta form and the suspension is stirred at 50° C. for 22 hours.

The product is isolated by filtration.

Perindopril L-arginine (9 g) is obtained in a yield of 73% relative to the perindopril. The HPLC quality of the isolated product is greater than 99%.

EXAMPLE 9

L-Arginine Salt of Perindopril—Starting from Perindopril Tert-Butylamine, in a Binary Mixture of Ethyl Acetate/DMSO 55/45, with Seeding Load perindopril erbumine (200 g, 1 eq.), methyltetrahydrofuran (700 g) and methanesulphonic acid (43.5 g, 1 eq.) into a reactor.

Filter off the insoluble material and add L-arginine (78.8 g, 1 eq.) and DMSO (500 g) to the solution.

Distil off the methyltetrahydrofuran and heat at 70° C. for 1 hour.

Add ethyl acetate (600 g) and seed with 2% of perindopril arginine in the delta crystalline form.

Cool to 25° C. over 4 hours, filter and wash the product with a mixture of ethyl acetate/DMSO.

Perindopril L-arginine (217 g, seed subtracted) is obtained in a yield of 88% relative to the perindopril. The HPLC quality of the product isolated is greater than 99%.

The filtration rate of the mother liquors is more than 1500 kg/h/m².

EXAMPLE 10

L-Arginine Salt of Perindopril—Starting from Perindopril (Free Acid), in a Ternary Mixture of Acetonitrile/DMSO/Toluene 45/50/5, with Seeding Load lyophilised perindopril (30 g, 1 eq.), DMSO (100 g) and L-arginine (13.8 g, 1 eq.) into a reactor. The mixture is heated at 70° C. for 2 hours.

Add a mixture of acetonitrile (90 g) and toluene (10 g) and seed with 2% of perindopril arginine in the delta crystalline form. The suspension is stirred at 70° C. for 2 hours.

Cool to 25° C. over 4 hours, filter and wash the product with acetonitrile and DMSO.

Perindopril L-arginine (41 g, seed subtracted) is obtained in a yield of 92% relative to the perindopril. The HPLC quality of the isolated product is greater than 99%.

The filtration rate of the mother liquors is more than 1500 kg/h/m².

COMPARISON EXAMPLE A

Adaptation of the Procedure of Example 3 of EP 1 279 665 to Obtaining the L-Arginine Salt of Perindopril The reactor is cooled to 0° C. beforehand. N-[1-(S)-ethoxycarbonyl-butyl]-(S)-alanine (80 g-1 eq.) and dichloromethane (1325 g, d=1.325) are introduced. N,N'-carbonyldiimidazole (71.5 g-1.2 eq.) and 0.336 L of dichloromethane are added to the mixture. The temperature of the mixture is brought to −5° C. prior to adding (2S,3aS,7aS)-2-carboxyperhydroindole (81 g-1.3 eq.). After a contact time of 2 hours 30 minutes, the mixture is dried and then taken up in water (1200 g, d=1.00). After acidification of the aqueous phase (with 185 ml of 4N HCl solution), the solution is extracted with dichloromethane (2517.5 g, d=1.325) and the aqueous phase is saturated with NaCl. The organic phase is dried and the residue from drying is taken up in ethyl acetate (1176.6 g, d=0.902). L-arginine is then added (68 g-1.06 eq.) and the mixture is held at 50° C. overnight, with stirring.

Filtration of the mixture is found to be impossible because the solid has a sticky consistency.

The solid is removed from the reactor by dismantling of the tank.

Yield (determined by titration): 1.6%.

COMPARISON EXAMPLE B

According to Example 6 of Patent Application WO 2009/157018

Perindopril (30 g) and L-arginine (13.8 g) are suspended in toluene (130 g, d=0.867) at ambient temperature. The mixture is refluxed for one hour. Then acetonitrile (1180.5 g, d=0.787) is added at 80° C. After maintaining stirring for one hour at that temperature, the suspension is filtered using a cell under 0.3 bar of nitrogen.

The average filtration rate of the mother liquors was measured at 100 kg/h/m². The product isolated has a sticky consistency and is pale pink in colour. The yield by weight is 46.5%. The HPLC quality of the product isolated is of the order of 83%.

The invention claimed is:

1. A process for the preparation of perindopril L-arginine salt of formula (I):

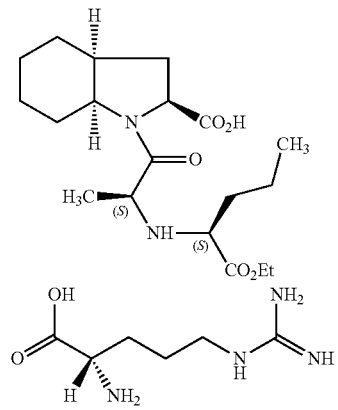

(I)

by means of reaction between perindopril and L-arginine in a solvent system selected from the group consisting of:
a binary mixture of acetonitrile and dimethyl sulphoxide,
a binary mixture of ethyl acetate and dimethyl sulphoxide, and
a ternary mixture of acetonitrile, dimethyl sulphoxide and toluene,
at a temperature from 10 to 100° C.,
followed by isolation by means of filtration of the L-arginine salt thereby obtained.

2. The process according to claim 1, wherein the perindopril is obtained by reaction of N-[1-(S)-ethoxycarbonyl-butyl]-(S)-alanine of formula (II):

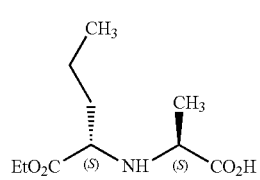

(II)

with an activation agent of formula $X_2C=O$ wherein X represents a leaving group,
in an organic solvent or a system of organic solvents,
at a temperature from −20 to 80° C.,
followed by reaction of the intermediate compound of formula (III) thereby obtained:

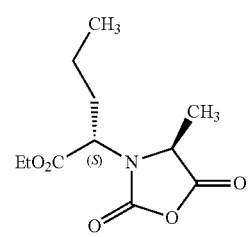

(III)

with (2S,3aS,7aS)-2-carboxyperhydroindole,
at a temperature from 0 to 80° C.

3. The process according to claim 2, wherein the activation agent is carbonyldiimidazole, phosgene, triphosgene, (1,1'-carbonyldi(1,2,4-triazole) or di(N-succinimidyl)carbonate.

4. The process according to claim 3, wherein the activation agent is carbonyldiimidazole and the amount of N,N'-carbonyldiimidazole is between 0.8 and 1.2 moles, inclusive, per mole of N[1-(S)-ethoxycarbonyl-butyl]-(S)-alanine.

5. The process according to claim 2, wherein the amount of (2S,3aS,7aS)-2-carboxyperhydroindole is between 0.8 and 1.2 moles, inclusive, per mole of N-[1-(S)-ethoxycarbonyl-butyl]-(S)-alanine.

6. The process according to claim 3, wherein the amount of (2S,3aS,7aS)-2-carboxyperhydroindole is between 0.8 and 1.2 moles, inclusive, per mole of N-[1-(S)-ethoxycarbonyl-butyl]-(S)-alanine.

7. The process according to claim 4, wherein the amount of (2S,3aS,7aS)-2-carboxyperhydroindole is between 0.8 and 1.2 moles, inclusive, per mole of N-[1-(S)-ethoxycarbonyl-butyl]-(S)-alanine.

8. The process according to claim 1, wherein the perindopril is obtained desaltification of perindopril tort-butylamine by the action of an acid.

* * * * *

UNITED STATES PATENT AND TRADEMARK OFFICE
CERTIFICATE OF CORRECTION

| | | |
|---|---|---|
| PATENT NO. | : 8,865,915 B2 | Page 1 of 1 |
| APPLICATION NO. | : 13/733353 | |
| DATED | : October 21, 2014 | |
| INVENTOR(S) | : Julie Linol et al. | |

It is certified that error appears in the above-identified patent and that said Letters Patent is hereby corrected as shown below:

Title page, Column 2, Foreign Patent Documents: "EP 1664937" should be -- EP 1864937 --.

In the Claims

Column 9, Line 2, Claim 3: "carbonyldiimidazole" should be -- N, N'-carbonyldiimidazole --.

Column 9, Line 5, Claim 4: "carbonyldiimidazole" should be -- N, N'-carbonyldiimidazole --.

Column 9, Line 21 and 22, Claim 8: "tort-butylamine" should be -- tert-butylamine --.

Signed and Sealed this
Twelfth Day of May, 2015

Michelle K. Lee
*Director of the United States Patent and Trademark Office*